United States Patent [19]

Swope et al.

[11] Patent Number: 5,350,697
[45] Date of Patent: Sep. 27, 1994

[54] SCATTERED LIGHT DETECTION APPARATUS

[75] Inventors: C. Hermas Swope, Raleigh; John G. Link; Jones M. Hyman, both of Durham, all of N.C.

[73] Assignee: Akzo N.V., Arnhem, Netherlands

[21] Appl. No.: 574,184

[22] Filed: Aug. 28, 1990

[51] Int. Cl.⁵ .......................................... G01N 33/552
[52] U.S. Cl. .................................... 436/527; 356/246; 356/338; 356/340; 356/342; 422/82.05; 422/82.09; 435/808; 436/164; 436/524; 436/805
[58] Field of Search ............... 422/82.05, 82.09; 436/524, 527, 805, 164; 356/246, 318, 336, 338, 340, 342; 435/808

[56] References Cited

U.S. PATENT DOCUMENTS

| | | | |
|---|---|---|---|
| 3,872,312 | 3/1975 | Hirschfeld | 250/461.2 |
| 3,905,767 | 9/1975 | Morris et al. | 422/82.05 |
| 4,704,029 | 11/1987 | Van Heuvelen | 436/95 |
| 4,952,055 | 8/1990 | Wyatt | 356/343 |
| 5,017,009 | 5/1991 | Schutt et al. | 356/338 |

FOREIGN PATENT DOCUMENTS 0254430  1/1988  European Pat. Off. .

OTHER PUBLICATIONS

Handbook of Chemistry and Physics, 67th Edition, 1986–1987, CRC Press pp. E-369 and E-372.

Primary Examiner—Esther M. Kepplinger
Assistant Examiner—Christopher L. Chin
Attorney, Agent, or Firm—William M. Blackstone; John W. Schneller

[57] ABSTRACT

An apparatus in which scattered light is measured, said apparatus having a light source aligned to direct illumination toward an interface between a sample container and an aqueous solution at an angle less than the critical angle. A detector to measure the scattered light is located at a place outside the envelope of the critical angle.

9 Claims, 3 Drawing Sheets

SCATTERED LIGHT DETECTION APPARATUS

FIELD OF THE INVENTION

This invention relates to an apparatus and immunoassay method that use scattered light detection.

TECHNOLOGY REVIEW

In known systems that detect ligands bound to the surface of an optically transparent substrate using changes in light effected by reactions on the surface of the optically transparent material, light is directed toward the interface at an angle equivalent to or greater than the critical angle. This configuration results in total internal reflectance, producing an evanescent wave.

Usually, the evanescent wave is established in an aqueous solution containing the specimen to be analyzed as a result of total internal reflectance within the optically transmissive solid material. For example, U.S. Pat. No. 3,939,350 to Kronick et al. uses a system in which ligands are bound to fluorescent labels, and a light source provides light at an appropriate wave length to activate the fluorescent molecules, which absorb the light. The light emitted from the device is measured and the level of absorption is indicative of the quantity of reactant in the specimen. The light is directed toward the liquid/solid interface at an angle that provides total internal reflection at the interface. An alternative method is described in which the activated fluorescent molecules emit light as the result of light energy penetrating a short distance past the transparent wall of the light transmissive material, i.e., the evanescent wave, where the light produced by fluorescence is detected as an indication of the presence of fluorescent molecules at the interface.

European patent application 82 201 107.8 describes a method and apparatus that measure the quantity of a ligand in a specimen using a wave guide immersed in the specimen, in which the optically transmissive material is the wave guide immersed within the specimen rather than used as the container or part of the container for the specimen. The modification of light passing through the wave guide is produced through multiple total internal reflection by reactants bound to the surface of the wave guide. The bound reactants change the light exiting from the wave guide as a result of the evanescent wave interacting with the reactant layer at the solid/liquid interface.

European patent application 85 304172.1 teaches a method of optical analysis that uses light passing from the liquid at the liquid/solid interface into the wave guide by total internal reflectance. The light exiting from the wave guide is measured.

European patent application 85 304496.4 describes a method for detecting ligands in a solution by directing light scattered at the interface of the aqueous solution and a solid substrate. The light is directed through the liquid toward the solid surface, on which immunoreactive ligands are placed in the pattern of a grating. Reactants in the solution, preferably labeled with light scattering particles, cause light to reflect at a certain angle when bound to reactants on the grating, which is measured by a light detector.

European patent application 87 305669.1 published Jan. 27th, 1988, describes an immunoassay system for detecting ligands or ligand bonding partners in solution in a heterogeneous format by detecting light scattered back from an evanescent wave disturbed by the presence of a colloidal gold label at the interface of a cuvette and the aqueous sample. The colloidal gold label is bound to an antibody reactive with antigens located on the surface of the sample cuvette. The evanescent wave existing at the interface is the result of a totally internally reflected incident light wave achieved by selecting the container, e.g., sample cuvette, to have a refractive index greater than that of the aqueous sample and aligning the light source and cuvette such that the illumination is directed toward the interface of the container and the aqueous solution at an angle equal to or greater than the critical angle. Light scattered at the interface is detected by a photodetector means placed such that only light scattered back toward the light source is detected. The location of the light source to provide illumination directed toward the interface at an angle greater than or equal to the critical angle is selected to achieve total internal reflectance, i.e., no penetration of the light into the specimen, thereby relying on an evanescent wave in the specimen to scatter back light for detection. If the incident light wave is totally internally reflected, it creates an evanescent wave at the specimen cuvette interface.

It is an object of the present invention to provide a new immunoassay method that introduces more light energy into the sample, and an apparatus that demonstrates a high level of sensitivity. The immunoassay method and apparatus of the present invention avoid the problem of low sensitivity, and provide the following advantages. By allowing more light to penetrate the receiving means, a stronger light signal is generated, and sensitivity is improved for detecting ligands and ligand binding partners in aqueous solutions.

SUMMARY OF THE INVENTION

Method and apparatus are provided for carrying out scattered light detection immunoassays.

The apparatus is comprised of an optically transmissive means for receiving an aqueous specimen solution, an illumination means, a means for directing illumination, an alignment means, and a photodetector means. Illumination is directed toward the interface of the optically transmissive means for receiving an aqueous solution and the aqueous solution at an angle less than the critical angle, that is, at an angle within the envelope of the critical angle. A photodetector means to measure scattered light is located outside the envelope of the critical angle. Preferably it is located beyond the envelope of the critical angle such that it receives light scattered beyond the critical angle, forward scattered light. It may also be located before the critical angle and in front of the light source where it will receive backward scattered light.

A method for determining the presence and quantity of a ligand in the aqueous solution by measuring scattered light is provided that comprises combining an aqueous specimen believed to contain a ligand of interest with having a light scattering particle label to form an aqueous specimen solution. A second liquid binding partner is bound to at least one inside surface of a means for receiving the sample made from an optically transmissive material having a refractive index greater than that of the aqueous solution. On introducing the aqueous solution into the sample receiving means, either before or after combining the specimen with the labelled first liquid binding partner an interface is formed between the aqueous solution and the optically transmissive material, and the interface is illuminated at an angle less than the critical angle.

DETAILED DESCRIPTION OF THE INVENTION

Figure 1:
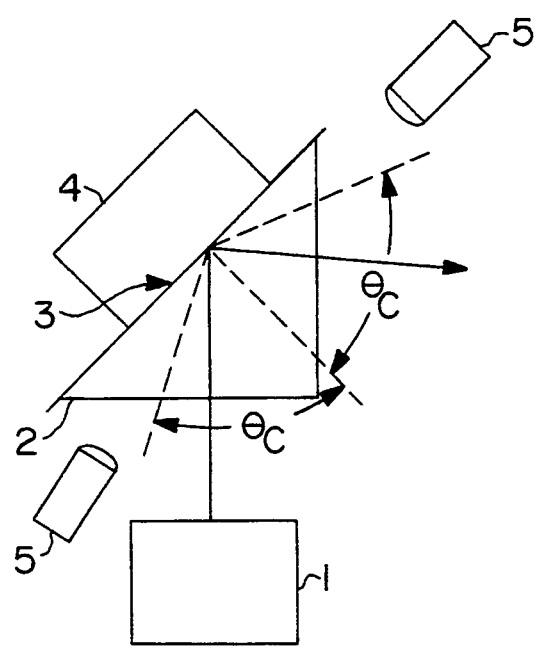
FIG. 1 represents an apparatus as provided by the present invention. A means for illumination 1 is aligned, so that a means for directing illumination 2 directs the light toward an interface 3 between a sample receiving means 4 and an aqueous solution at an angle less than the critical angle. A photodetector means 5 is located outside the envelope of the critical angle, either beyond the critical angle or, before the means for illumination.

An apparatus is provided for use in an immunoassay for detecting a ligand or a ligand binding partner in an aqueous solution using a ligand binding partner labelled with a light scattering particle and a ligand binding partner bound to the surface of a means for receiving an aqueous solution. The apparatus comprises:

(a) a receiving means for receiving an aqueous solution constructed at least in part of an optically transmissive material, wherein the optically transmissive material has a refractive index greater than that of the aqueous solution;

(b) illumination means for providing illumination to the interface between said optically transmissive receiving means and the aqueous solution;

(c) alignment means for positioning said optically transmissive receiving means in a fixed relationship to the illumination means such that the illumination is directed toward the interface at an angle less than the critical angle; and (d) photodetector means for receiving light scattered by the light scattering particle.

The apparatus may further comprise means for directing said illumination toward said interface.

Examples of receiving means include sample containers, capillary tubing, cuvettes, and microscope slides.

Examples of means for providing illumination include any monochromatic or polychromatic light source and lasers. The means for providing illumination is aligned such that the illumination is directed toward the interface between the receiving means and the aqueous solution at an angle less than the critical angle. The means for directing the illumination may be inherently part of the illuminization means, such as in a laser, or may be a separate unit such a lens, prism or mirror.

The critical angle is defined as the angle at which light directed toward the interface formed by the aqueous sample and receiving means results in total internal reflectance of the light within the receiving means. Using a light source at an angle less than the critical angle results in transmission of light at the interface, resulting in transmitted light being scattered by the light scattering particles. By contrast, the prior art methods depended on total internal reflection by which the light scattered is evanescent light. The amount of light energy transmitted is greater than that available in an evanescent wave and thus the present invention using transmitted light provides greater sensitivity than any previous method. Preferably, forward scattered light is detected using a photodetector located beyond the envelope of the critical angle. Detection from beyond the critical angle prevents light scattered by the bulk medium from reaching the detector, and only light scattered from the light scattering particles at the interface, such as gold sol particles, is observed. Optionally, the photodetector may be located before the critical angle and before the light source to measure backscattered light. Measured increases in scattered light resulting from light scattering particles bound via the ligand and ligand binding partners to the interface indicate the amount of ligand in the specimen.

An immunoassay method is provided to qualitatively or quantitatively detect the presence of a ligand in an aqueous solution comprising the steps of:

(a) providing a first ligand binding partner specific for the ligand in the aqueous solution, the first ligand binding partner being labeled directly or indirectly with a particle having light scattering characteristics in an aqueous solution;

(b) combining the first ligand binding partner, the aqueous specimen and a second binding partner bound to the inside surface of a sample receiving means made at least in part from an optically transmissive material to form an interface between the optically transmissive material and the sample, preferably using a plurality of first and second ligand binding partners capable of binding to the ligand, the optically transmissive material having a refractive index greater than the refractive index of the aqueous solution;

(c) illuminating the interface through the optically transmissive material at an angle less than the critical angle; and (d) measuring the amount of light scattered from the interface, wherein the amount of scattered light is a function of the amount of ligand present in the aqueous solution. The scattered light measured may be light scattered from the interface at greater than the critical angle by locating a detector at a position beyond the envelope of the critical angle.

Preferably, the method comprises introducing the sample solution into a receiving means that had previously been coated with a reagent containing the second binding partner. The first ligand binding partner bound to light scattered particles is introduced after removal of excess sample solution and, optionally, washing. In the preferred embodiment the optically transmissive receiving means is a cuvette. As the reaction on the surface of the optically transmissive material proceeds, the scattered light signal is monitored and the result of the assay is determined by computing the time rate of change or comparing the level measured against a standard or a reference. The rate of signal change or the time for the signal to reach a predetermined value is reported as the measure of the amount of ligand present.

EXAMPLE 1

An apparatus according to the invention for carrying out immunoassays was constructed comprising a polystyrene cuvette in the form of a microtitre well coupled to a glass prism with optical immersion oil. A helium neon laser was used to illuminate part of the cuvette's bottom surface at an angle less than the critical angle. The critical angle was calculated to be 57.074°. The prism, aqueous solution, polystyrene cuvette, and optical immersion oil, had refractive indexes of 1.64. 1.33, 1.59, and 1.51, respectively. The microtitre wells were coated with Anti-HBsAg immune monoclonal antibodies. The samples were

| Negative | Normal Human Serum Pool (negative for HbsAg) |
|----------|-----------------------------------------------|
| Positive | NML Elisa Positive Control (contains approx. 280/ng/ml HBsAg) |

Figure 2:
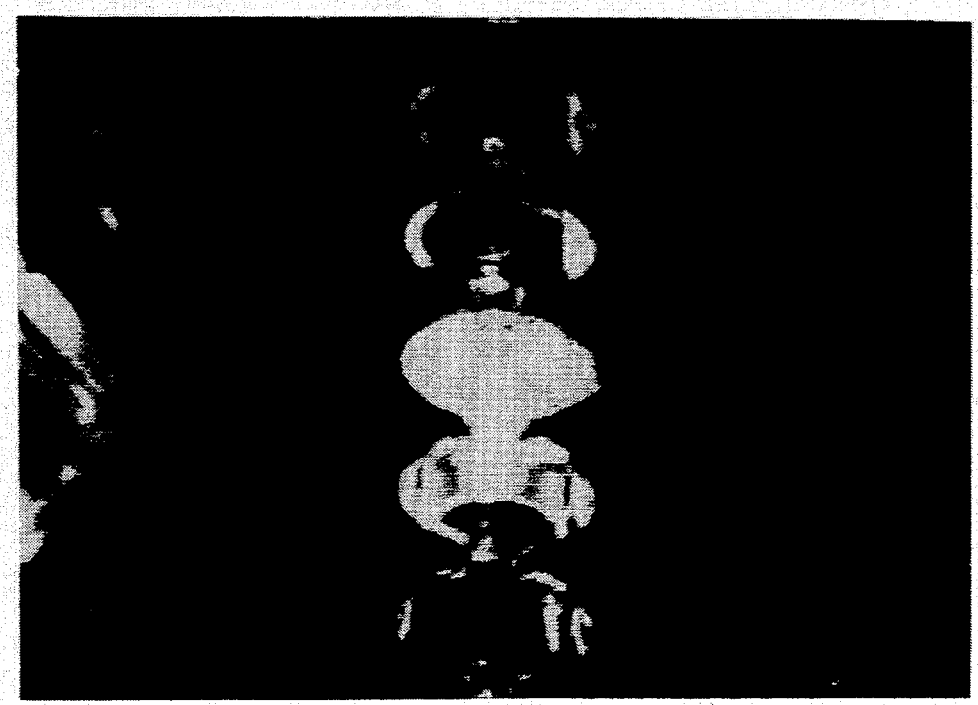
FIG. 2 illustrates a positive reaction with light scattered by reactants.
Figure 3:
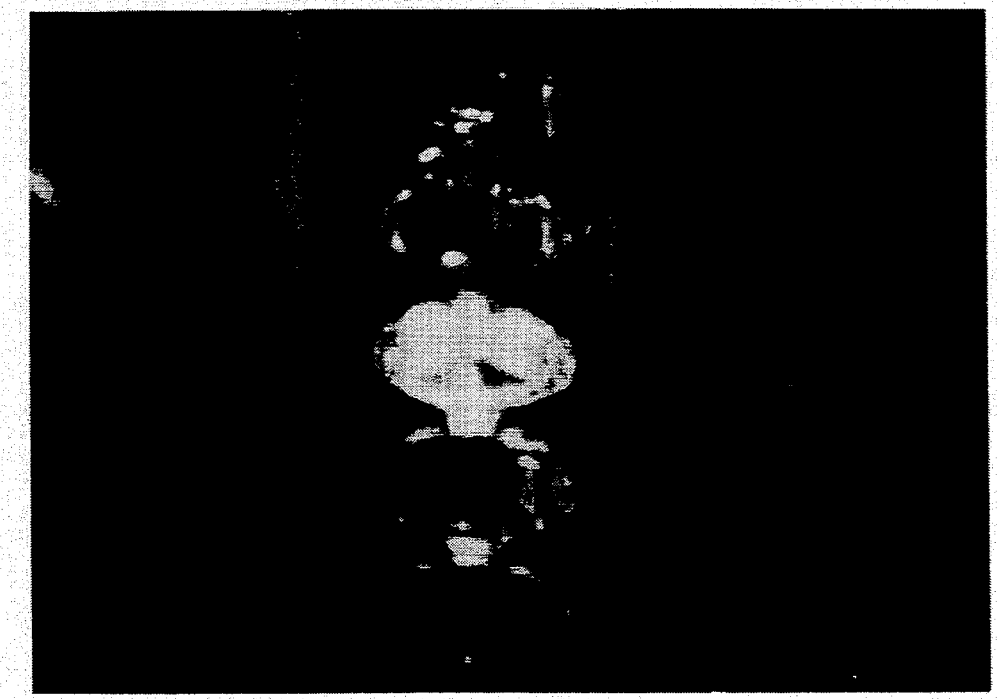
FIG. 3 illustrates a negative reaction in which the absences of reactants with light scattering particles results in no light being scattered.

The experiment performed was qualitative. The photographic record shown in FIG. 2 demonstrated the presence of light scattered by the reactants. FIG. 3 shows photos illustrating no reaction indicating a clear difference in the amount of light scattered, which is detected by the camera. The area indicated by the arrow is the bottom of the microliter plate well on which the captured antibodies were bound. FIG. 2 illustrates a positive example with scattered light. FIG. 3 is a negative example showing no scattered light. In an alternative embodiment, and a preferred embodiment for practicing the invention, the camera is replaced by the appropriate electronic photodetector.

While the invention has been described in connection with specific embodiments thereof, it will be understood that it is capable of further modification. This application is intended to cover any variations, uses, or adaptations of the invention following, in general, the principles of the invention and including such departures from the present disclosure as come within known or customary practice within the art to which the invention pertains and as may be applied to the essential features set forth herein, within the scope of the appended claims.

What is claimed is:

1. An apparatus for conducting an immunoassay to detect an analyte ligand using a ligand labelled with light scattering particles or a first ligand binding partner labelled with light scattering particles in an aqueous solution, comprising:

(a) a receiving means for receiving and holding an aqueous solution, said receiving means coated with a reagent containing a second ligand binding partner for said analyte ligand or said ligand labelled with light scattering particles and including at least one portion consisting of an optically transmissive material, said material having a refractive index greater than that of said aqueous solution;

(b) illumination means for providing light to an interface formed between said optically transmissive material portion of the receiving means and an aqueous solution in said receiving means, wherein the light is directed to strike the interface at an angle less than the critical angle; and (d) photodetector means for receiving light scattered from said interface at an angle equal to or greater than the critical angle by bound light scattering particles.

2. The apparatus as recited in claim 1, wherein said photodetector means detects forward scattered light.

3. The apparatus as recited in claim 1, wherein said receiving means is a sample container.

4. The apparatus as recited in claim 1, wherein said receiving means is a cuvette.

5. The apparatus as recited in claim 1, wherein said illumination means is a laser.

6. The apparatus as recited in claim 1, further comprising an alignment means for positioning said optically transmissive material portion in a fixed relationship to the illumination means, wherein the light is directed to strike the interface at an angle less than the critical angle by said alignment means.

7. The apparatus as recited in claim 6, wherein said alignment means is a prism.

8. The apparatus as recited in claim 1, wherein said receiving means is a slide with said aqueous solution on one surface of said slide, and wherein said illumination is directed through said slide from the other side.

9. The apparatus as recited in claim 1, wherein said photodetector means detects back scattered light.

* * * * *

UNITED STATES PATENT AND TRADEMARK OFFICE
CERTIFICATE OF CORRECTION

PATENT NO. : 5,350,697
DATED : September 27, 1994
INVENTOR(S) : C. Hermas SWOPE, John G. LINK, and Jones M. HYMAN It is certified that error appears in the above-indentified patent and that said Letters Patent is hereby corrected as shown below:

Please correct claim 1 as follows:

Column 6, Line 15, before "photodetector" delete "(d)" and substitute therefor -- (c) -- .

Signed and Sealed this

Fourteenth Day of February, 1995

Attest:

BRUCE LEHMAN

Attesting Officer     Commissioner of Patents and Trademarks